(12) United States Patent
Dudnyk et al.

(10) Patent No.: US 12,180,386 B2
(45) Date of Patent: Dec. 31, 2024

(54) COATED DEVICES AND RELATED METHODS

(71) Applicant: Covalon Technologies Inc., Mississauga (CA)

(72) Inventors: Vyacheslav Dudnyk, Mississauga (CA); Valerio DiTizio, Toronto (CA)

(73) Assignee: COVALON TECHNOLOGIES INC., Mississauga (CA)

( * ) Notice: Subject to any disclaimer, the term of this patent is extended or adjusted under 35 U.S.C. 154(b) by 243 days.

(21) Appl. No.: 16/900,332

(22) Filed: Jun. 12, 2020

(65) Prior Publication Data

US 2020/0392371 A1 Dec. 17, 2020

Related U.S. Application Data (60) Provisional application No. 62/861,995, filed on Jun. 14, 2019.

(51) Int. Cl.
| | |
|---|---|
| *C09D 175/04* | (2006.01) |
| *A61L 29/04* | (2006.01) |
| *A61L 29/08* | (2006.01) |
| *A61L 29/16* | (2006.01) |

(52) U.S. Cl.
CPC .......... *C09D 175/04* (2013.01); *A61L 29/049* (2013.01); *A61L 29/085* (2013.01); *A61L 29/16* (2013.01); *A61L 2300/104* (2013.01); *A61L 2300/404* (2013.01); *A61L 2420/02* (2013.01)

(58) Field of Classification Search
CPC .... A61M 25/00; C09D 175/04; A61L 29/049; A61L 29/085; A61L 29/16; A61L 29/08; A61L 27/00
See application file for complete search history.

(56) References Cited

U.S. PATENT DOCUMENTS

| | | | |
|---|---|---|---|
| 4,585,666 A * | 4/1986 | Lambert | ................ C08J 7/0427 427/412.5 |
| 6,808,738 B2 | 10/2004 | DiTizio et al. | |
| 8,697,112 B2 | 4/2014 | Dudnyk et al. | |
| 8,746,168 B2 | 6/2014 | Abbasian et al. | |
| 8,840,927 B2 | 9/2014 | DiTizio et al. | |
| 8,877,256 B2 | 11/2014 | Dudnik et al. | |
| 8,920,886 B2 | 12/2014 | Abbasian et al. | |
| 8,967,077 B2 | 3/2015 | Abbasian et al. | |

(Continued)

FOREIGN PATENT DOCUMENTS

| | | |
|---|---|---|
| EP | 2 796 155 A1 | 10/2014 |
| WO | WO 2011/038483 A1 | 4/2011 |

OTHER PUBLICATIONS

Aflori et al., Bactericidal effect on Foley catheters obtained by plasma and silver nitrate, 2015, High Performance Polymers, vol. 27, No. 5, 655-660 (Year: 2015).*

(Continued)

*Primary Examiner* — Dah-Wei D. Yuan
*Assistant Examiner* — Andrew J Bowman
(74) *Attorney, Agent, or Firm* — Alston & Bird LLP (57) ABSTRACT

Provided herein is a method of grafting a polymeric coating onto a first side of a wall of a device. The method comprises: applying an initiator substantially only to a second side of the wall; applying a coating composition to the first side of the wall; and graft-polymerizing the coating composition.

22 Claims, 1 Drawing Sheet

(56) References Cited

U.S. PATENT DOCUMENTS

| | | | |
|---|---|---|---|
| 2005/0131356 A1* | 6/2005 | Ash | A61L 31/16 604/500 |
| 2011/0104390 A1 | 5/2011 | Abbasian et al. | |
| 2013/0158488 A1* | 6/2013 | Weaver | A61L 29/14 427/2.3 |
| 2018/0296737 A1 | 10/2018 | Sivakumaran et al. | |

OTHER PUBLICATIONS

WIPO Application No. PCT/UCA2020/050819, PCT International Search Report and Written Opinion of the International Searching Authority mailed Sep. 1, 2020.
WIPO Application No. PCT/UCA2020/050819, PCT International Preliminary Report on Patentability mailed Dec. 14, 2021.

* cited by examiner

Figure 1

COATED DEVICES AND RELATED METHODS

FIELD

The present invention relates to polymeric coatings. More specifically, the present invention is, in aspects, concerned with coated devices and methods of coating devices with polymeric coatings.

BACKGROUND

Modern medical devices are often composed of polymers that are generally well tolerated by the human body and for this reason, along with their flexibility and chemical stability, polymer-based medical devices are widely used in current clinical practice. Methods of coating such devices are known and generally comprise immersing or submerging the device in various solutions in a step-wise fashion.

For example, U.S. Pat. Nos. 6,808,738 and 8,840,927 describe a method for the modification of the surfaces of polymeric materials with polymer coatings that may be subsequently treated to be lubricious and anti-microbial. The method comprises incubating a photo-initiator-coated polymeric material with an aqueous monomer that is capable of free radical polymerization and exposing the incubating polymeric material to UV light creating a modified surface on said polymeric material U.S. Pat. No. 8,877,256 describes an antimicrobial photostable coating composition that deters photo-induced discoloration, does not stain tissue and can be applied to the surface of a variety of medical materials. The composition comprises in an aspect silver-PCA complex and dye.

U.S. Pat. No. 8,697,112, describes a method for treating a surface with a therapeutic agent. The method comprises precipitating a therapeutic agent from a hydrophilic polymeric base layer with which the therapeutic agent has been complexed, to form a layer comprising microparticles of the therapeutic agent on the hydrophilic polymeric base layer, the hydrophilic polymeric base layer being grafted to the surface.

U.S. Pat. Nos. 8,746,168, 8,920,886, and 8,967,077 describe a system and method for photo-grafting a coating polymer onto the surface of a medical device. The system comprises a plurality of stations including a novel grafting station. The system and method of the invention are both time- and resource-efficient. The system includes several stations, each station including a dipping tank. The system allows for the automated, semi-automated, or manual dipping of medical devices into the dipping tanks in a specified order, as desired, wherein at least one of the stations is a grafting station for photo-grafting the coating polymer onto the surface of the medical device.

U.S. Patent Application Publication No. 2018/0296737 describes a coating composition comprising an aqueous solution comprising at least one vinyl carboxylic acid monomer and at least one neutral monomer, wherein the at least one neutral monomer has a glass transition temperature of less than about 100° C. in homopolymeric form.

There is a need for alternative methods to overcome or mitigate at least some of the deficiencies of the prior art, or to provide a useful alternative.

SUMMARY

In accordance with an aspect there is provided a method of grafting a polymeric coating onto a first side of a wall of a device, the method comprising:

applying an initiator substantially only to a second side of the wall;

applying a coating composition to the first side of the wall; and graft-polymerizing the coating composition.

In an aspect, the method further comprises applying the coating composition to the second side of the wall before the polymerizing step.

In an aspect, the device comprises a lumen defined by the wall, wherein the first side of the wall faces away from the lumen and the second side of the wall faces into the lumen.

In an aspect, applying the initiator substantially only to a second side of the wall comprises aspirating the initiator into the lumen and subsequently expelling the initiator from the lumen.

In an aspect, applying the initiator substantially only to a second side of the wall for a time of from about 1 second to about 30 minutes, such as from about 10 seconds to about 10 minutes, such as about 1 minute.

In an aspect, the initiator is a photoinitiator.

In an aspect, the photoinitiator is selected from the group consisting of a perester, an α-hydroxyketone, a benzil ketal, a benzoin, derivatives thereof, and mixtures thereof.

In an aspect, the photoinitiator is selected from tert-butylperoxybenzoate and/or benzophenone.

In an aspect, the initiator is in solution in an organic solvent such as alcohol, such as ethanol.

In an aspect, applying the coating composition to the first side of the wall comprises applying the coating composition to the first and second sides of the wall.

In an aspect, applying the coating composition to the first and second sides of the wall comprises immersing the device in the coating composition.

In an aspect, the coating composition comprises one or more monomers.

In an aspect, the one or more monomers comprise at least one vinyl carboxylic acid monomer and at least one neutral monomer.

In an aspect, the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof.

In an aspect, the neutral monomer is selected from the group consisting of acrylates, such as methyl acrylate, methacrylates, such as methyl methacrylate, acrylamides, methacrylamides, vinyl compounds, and combinations thereof.

In an aspect, the vinyl carboxylic acid comprises acrylic acid and the neutral monomer comprises methyl acrylate.

In an aspect, the composition comprises the vinyl carboxylic acid monomer in an amount of from about 20% to about 95% by weight and/or in an amount of from about 100 mM to about 500 mM, such as about 300 mM.

In an aspect, the composition comprises the neutral monomer in an amount of from about 5% to about 80% by weight and/or in an amount of from about 10 mM to about 250 mM, such as about 50 mM.

In an aspect, the graft-polymerizing step comprises applying UV light to the device.

In an aspect, UV light is applied to the device for from about 1 to about 10 minutes, such as about 3 minutes.

In an aspect, the graft-polymerizing step further comprises bubbling an inert gas such as nitrogen through the composition, before and/or during the step of applying UV light to the device.

In an aspect, the bubbling the inert gas is for from about 1 to about 10 minutes, such as about 6 minutes.

In an aspect, the method further comprises ionizing the coating after the polymerizing step.

In an aspect, ionizing the coating comprises applying a basic solution to the coating.

In an aspect, the basic solution has a pH of greater than about 8.0.

In an aspect, the basic solution is selected from the group consisting of TRIZMA base, disodium tetraborate, sodium carbonate, and hydroxides such as ammonium hydroxide, calcium hydroxide, sodium hydroxide, and mixtures thereof.

In an aspect, ionizing the coating comprises soaking the device in the basic solution for a time of from about 1 minute to about 30 minutes, such as about 6 minutes.

In an aspect, the method further comprises applying an antimicrobial agent to the coating after the step of ionizing the coating.

In an aspect, the step of applying the antimicrobial agent comprises soaking the device in a solution comprising the antimicrobial agent for a time of from about 1 to about 30 minutes, such as from about 3 to about 5 minutes.

In an aspect, the antimicrobial agent is selected from the group consisting of chlorhexidine, octenidine, ethonium, benzalkonium chloride, benzethonium chloride, polyhexamethylene biguanide, copper, zinc, silver, chlorine, fluoroquinolones, b-lactams, macrolides, aminoglycosides, tetracyclines, and combinations thereof.

In an aspect, the antimicrobial agent comprises silver ions.

In an aspect, the silver ions are derived from a silver salt selected from the group consisting of silver phosphate, silver citrate, silver lactate, silver acetate, silver benzoate, silver chloride, silver carbonate, silver iodide, silver iodate, silver nitrate, silver laurate, silver sulfadiazine, silver sulfate, silver palmitate, and mixtures thereof In an aspect, the method further comprises applying a photostabilizer such as brilliant green and/or pyrrolidone carboxylic acid to the device.

In an aspect, the device is soaked in a solution comprising the photostabilizer, pyrrolidone carboxylic acid, and silver ions.

In an aspect, the method further comprises washing the device in a basic solution after the step of applying the antimicrobial agent.

In an aspect, the method further comprises protonating the coating after the polymerizing step.

In an aspect, protonating the coating comprises applying an acidic solution to the coating.

In an aspect, the acidic solution comprises an acid selected from the group consisting of HCl, HBr, HI, HClO4, H2SO4, HNO3, sodium hydrogen sulfate, sulfonic acid, acetic acid, phosphoric acid, phosphorous acid, sulfurous acid, trichloroacetic acid, salicylic acid, phthalic acid, nitrous acid, lactic acid, hydroiodic acid, formic acid, citric acid, tartaric acid, and combinations thereof.

In an aspect, the step of applying the acidic solution to the coating for a time of from about 1 to about 30 minutes, such as about 6 minutes.

In an aspect, the method comprises a step of washing the device in ethanol immediately after the step of polymerizing for a time of from about 1 minute to about 30 minutes, such as about 6 minutes.

In an aspect, the method comprises a final step of washing the device in deionized water and/an alcohol such as ethanol for a time of from about 1 minute to about 30 minutes, such as about 6 to about 10 minutes, such as about 6 minutes.

In an aspect, the method further comprises air drying the device.

In an aspect, the method further comprises sterilizing the device.

In an aspect, the coating:

a) is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours;

b) is inherently antithrombogenic, optionally showing a greater than about 80% reduction, such as a greater than about 85%, 90%, 95%, 96%, 97%, 98%, or 99% reduction, relative to an uncoated surface;

c) releases low or no particulates, optionally releasing fewer particulates than an uncoated surface;

d) is lubricious;

e) has high resistance to cracking when expanded or inflated; and/or f) has high resistance to delamination as demonstrated by the maintenance of hydrophilicity after exposure to high shear force.

In an aspect, exposure of the polymeric coating to an altered pH environment restores its inherent biological activity, such as antimicrobial activity, antithrombogenicity, low to no particulate release, lubricity, resistance to cracking, and/or maintenance of hydrophilicity.

In an aspect, the device is made from a material selected from the group consisting of polyurethanes, polyamides, polyesters, polycarbonates, polyureas, polyethers, polyorganosiloxanes, polysulfones, polytetrafluoroethylene, polysiloxanes, and combinations thereof.

In an aspect, the device is a medical device selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

In accordance with an aspect, there is provided a medical device made by the method described herein.

In accordance with an aspect, there is provided an initiator station for applying an initiator to a first side of a wall of a device, the initiator station comprising:

a tank for holding the initiator;

a support for holding the device so that, in use, substantially only a second side of the wall contacts the initiator.

In an aspect, the device comprises a lumen defined by the wall, wherein the first side of the wall faces away from the lumen and the second side of the wall faces into the lumen.

In an aspect, the method further comprises an aspirator for aspirating the initiator into the lumen.

In accordance with an aspect, there is provided a system for grafting a polymeric coating onto a first side of a wall of a device, the system comprising:

the initiator station described herein; and a grafting station comprising:

a grafting tank for applying a polymerizable solution to the first side of the wall; and a UV light source for exposing the device to UV light.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the FIGURES, in which.

DETAILED DESCRIPTION

Described herein, in aspects, are novel methods of coating medical devices, typically devices comprise a lumen, such as catheters. In conventional methods, a polymeric device such as a catheter would be immersed in an initiator solution so that both sides of a wall of the device (the lumen-facing wall and the exterior-facing wall) would be coated with the initiator. The device would then be immersed in a coating composition and subsequently subjected to graft-polymerization. It was believed that, in order to obtain efficient graft polymerization on both sides of the wall of the device, both sides of the wall of the device would have to be pretreated with the initiator. However, it has now been found that devices can be coated with initiator only on one wall of the device, immersed in a coating composition, and subsequently subjected to graft-polymerization in order to achieve efficient grafting of the coating composition on both sides of the wall. For example, in aspects, initiator aspirated into only the lumen of the device and, therefore, contacting substantially only the lumen-facing wall of the device, will be sufficient to achieve graft-polymerization of the coating onto the exterior-facing wall of the device. This improves efficiencies and reduces the volume of initiator that is required to be used in order to effectively graft-polymerize the coating composition onto one or both sides of the wall of the device.

Definitions

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded by way of proviso or negative limitation, such as any specific compounds or method steps, whether implicitly or explicitly defined herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Methods of Coating

Described herein are methods of grafting a polymeric coating onto a first side of a wall of a device, such as a polymeric medical device. The method comprises applying an initiator substantially only to a second side of the wall; applying a coating composition to the first side of the wall; and graft-polymerizing the coating composition.

It will be understood that the coating composition may further be applied to the second side of the wall before the polymerizing step, if it is desired that both sides of the wall of the device be coated. Without wishing to be bound by theory, it appears that application of the initiator to one wall is sufficient to allow graft polymerization to be achieved on both walls, wherever the coating composition is present. It is believed that the photoinitiator migrates through the wall and that this migration may be facilitated by the solvent in which the photoinitiator is dissolved. The coating composition may be applied to the entire device or to only the portions of the device that are desired to be coated. Typically, the device is immersed in the coating composition so that both the first and second sides of the wall are coated with the coating composition.

Typically, the device comprises a lumen defined by the wall, wherein the first side of the wall faces away from the lumen and the second side of the wall faces into the lumen. In this way, applying the initiator substantially only to a second side of the wall comprises applying the initiator to the lumen, such as by aspiration. The initiator may be allowed to drain from the lumen or may be actively expelled from the lumen.

The device is typically made from a material selected from the group consisting of polyurethanes, polyamides, polyesters, polycarbonates, polyureas, polyethers, polyorganosiloxanes, polysulfones, polytetrafluoroethylene, polysiloxanes, and combinations thereof. Typically, the device is a medical device selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

The initiator is typically applied to the device for a time of from about 1 second to about 30 minutes, such as from about 1, 5, 10, 15, 30, or 45 seconds, or 1, 2, 3, 4, 5, 6, 7, 8, 9, 10, 15, 20, or 25 minutes to about 5, 10, 15, 30, or 45 seconds, or 1, 2, 3, 4, 5, 6, 7, 8, 9, 10, 15, 20, 25, or 30 minutes, such as about 30 seconds, or 1, 2, 3, 4, 5, 6, 7, 8, 9, or 10 minutes. In typical aspects, the initiator is applied to the device for about 1 minute.

Application of the initiator substantially only to a second side of the wall of the device is typically accomplished by spraying, aspirating, dipping, or otherwise applying the initiator in a manner in which substantially only the second side of the wall is exposed. For example, when the initiator is aspirated into the lumen of a device such as a catheter, the tip of the catheter may be placed in a solution of the initiator which is then aspirated into the lumen of the catheter. It will be understood that a small amount of initiator may contact the first side of the wall of the device when the tip is immersed in the solution so that effective aspiration may be achieved.

Once the initiator is applied substantially only to the second side of the wall of the device, the device is typically placed into the coating composition immediately thereafter, such as without first drying the device.

In typical aspects, the initiator is a photoinitiator and is, for example, selected from the group consisting of a perester, an α-hydroxyketone, a benzil ketal, a benzoin, derivatives thereof, and mixtures thereof. In typical aspects, the photoinitiator is selected from tert-butylperoxybenzoate and/or benzophenone. The initiator is typically in solution in an organic solvent, such as alcohol, for example, ethanol.

The initiator is typically present in the organic solvent in an amount sufficient to initiate polymerization of the coating composition. This is typically from about 10 mM to about 250 mM, such as from about 10 mM, 25 mM, 50 mM, 75 mM, 100 mM, 150 mM, or 200 mM to about 25 mM, 50 mM, 75 mM, 100 mM, 150 mM, 200 mM, or 250 mM, such as about 50 mM.

The coating composition may be any coating composition known that is capable of polymerizing onto the surface of a polymeric device. For example, the coating composition may be the coating composition described in U.S. Pat. Nos. 6,808,738, 8,840,927, 8,877,256, 8,697,112, 8,746,168, 8,920,886, and/or 8,967,077 and/or U.S. Patent Application Publication No. 2018/029673713, each of which is incorporated herein by reference in its entirety.

Typically, the one or more monomers comprise at least one vinyl carboxylic acid monomer and at least one neutral monomer. For example, the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, 4-vinylbenzoic acid, and combinations thereof. For example, the neutral monomer is selected from the group consisting of acrylates, such as methyl acrylate, methacrylates, such as methyl methacrylate, acrylamides, methacrylamides, vinyl compounds, and combinations thereof. Typically, the vinyl carboxylic acid comprises acrylic acid and the neutral monomer comprises methyl acrylate.

In particular aspects, the at least one neutral monomer has a glass transition temperature ($T_g$) of less than that of a homopolymer of acrylic acid (about 105° C.), when in homopolymeric form. It has been found that specifically choosing a neutral monomer with a $T_g$ of less than a homopolymer of acrylic acid, such as less than about 105° C. or, more typically less than about 100° C., "softens" the mechanical properties of the coating (relative to a pure polyacrylic acid homopolymer, for example) allowing for some expansion, such as in Foley catheter balloon inflation, with low to no cracking and/or delamination. Thus, copolymers made using the neutral monomers described herein with a homopolymeric $T_g$ below that of polyacrylic acid possess sufficient flexibility to allow for expansion of inflatable materials with minimal or no cracking or delamination.

In certain aspects, therefore, the at least one neutral monomer has a glass transition temperature that is less about 105° C. or, in more specific aspects, of less than about 100° C., 90° C., 80° C., 70° C., 60° C., 50° C., 40° C., 30° C., 20° C., or 10° C. in homopolymeric form.

In this way, a copolymer formed from the polymerization of the at least one vinyl carboxylic acid monomer and the at least one neutral monomer typically has a glass transition temperature that is lower than about 100° C., such as less than about 90° C., 80° C., 70° C., 60° C., 50° C., 40° C., 30° C., 20° C., or 10° C.

It will be understood that the vinyl carboxylic acid monomer may be present in the coating composition and/or the polymeric coating in any amount, typically from about 20% to about 90% by weight, such as from about 20%, 25%, 30%, 35%, 40%, 45%, 50%, 55%, 60%, 70%, or 75% to about 25%, 30%, 35%, 40%, 45%, 50%, 55%, 60%, 70%, 75%, or 80% by weight. In additional or alternative aspects, the vinyl carboxylic acid monomer may be present in the coating composition and/or the polymeric coating in amounts of from about 100 mM to about 500 mM, such as from about 100 mM, 150 mM, 200 mM, 250 mM, 300 mM, 350 mM, 400 mM, or 450 mM to about 150 mM, 200 mM, 250 mM, 300 mM, 350 mM, 400 mM, 450 mM, or 500 mM, such as about 300 mM.

Likewise, the neutral monomer may be present in the coating composition and/or the polymeric coating in any amount, typically from about 10% to about 80% by weight, such as from about 10%, 15%, 20%, 25%, 30%, 35%, 40%, 45%, 50%, 55%, 60%, 70%, or 75% to about 15%, 20%, 25%, 30%, 35%, 40%, 45%, 50%, 55%, 60%, 70%, 75%, or 80% by weight. In additional or alternative aspects, the neutral monomer may be present in the coating composition and/or the polymeric coating in amounts of from about 10 mM to about 250 mM, such as from about 10 mM, 25 mM, 50 mM, 75 mM, 100 mM, 150 mM, or 200 mM to about 25 mM, 50 mM, 75 mM, 100 mM, 150 mM, 200 mM, or 250 mM, such as about 50 mM.

The vinyl carboxylic acid and the neutral monomer may be present in the coating composition in various ratios, such as from about 1:50 to about 50:1, such as from about 1:50, 1:40, 1:30, 1:20, 1:10, 1:9, 1:8, 1:7, 1:6, 1:5, 1:4, 1:3, 1:2, or 1:1 to 2:1, 3:1, 4:1, 5:1, 6:1, 7:1, 8:1, 9:1, 10:1, 20:1, 30:1, 40:1, or 50:1.

The coating composition may comprise additional excipients as would be understood to a skilled person.

Typically, after the coating composition is applied to one or more walls of the device as desired, the coating is then polymerized onto the device by applying UV light for a time of from about 10 seconds to about 30 minutes, such as from about 10, 15, 30, or 45 seconds, or 1, 2, 3, 4, 5, 6, 7, 8, 9, 10, 15, 20, or 25 minutes to about 15, 30, or 45 seconds, or 1, 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the UV light is applied to the device for about 3 minutes with or without agitation, while the device is submerged in the vinyl carboxylic acid monomers and the neutral monomers solution.

The polymerizing step typically includes purging or bubbling an inert gas such as nitrogen through the monomers, before and/or during the step of applying UV light to the device. The gas is typically bubbled before the UV light is applied and is typically for a time period of from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the gas is bubbled for about 6 minutes.

Typically, the vinyl carboxylic acid monomers and the neutral monomers are present in the same solution, however, it is contemplated that the initiator could be applied to the desired wall of the device, followed by application and/or immersion in one monomer solution and then the other, whereafter polymerization is effected.

Typically, after polymerizing the coating, the coating is washed with alcohol, such as ethanol, for a short period of time, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in ethanol, with or without agitation, for about 6 minutes.

After the alcohol wash, the coating is typically ionized by applying a basic solution to the coating. The basic solution typically has a pH of greater than about 7.0, 7.5, 8.0, 8.5, or 9.0. The basic solution may be any known basic solution but is typically selected from the group consisting of TRIZMA base, disodium tetraborate, sodium carbonate, and hydroxides such as ammonium hydroxide, calcium hydroxide, sodium hydroxide, and mixtures thereof, for example.

In typical aspects, ionizing the coating comprises soaking the device in the basic solution for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in the basic solution with or without agitation for about 6 minutes.

Once the coating is ionized, an therapeutic agent may be applied to the coating typically by soaking the device in a solution comprising the therapeutic agent for a time of from about 1 to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. Typically, the device comprising the ionized coating is soaked in a solution comprising the therapeutic agent with or without agitation for a time of from about 3 to about 5 minutes.

The therapeutic agent in aspects is an antimicrobial agent, including one or more antibacterial agents, and/or one or more antifungal agents, and/or one or more antiviral agents, and/or one or more antiseptic agents, and/or combinations thereof.

In typical aspects, the antimicrobial agent is an antibacterial agent. While any antibacterial agent may be used in the polymeric coatings described herein, some non-limiting exemplary antibacterial agents include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, metal salts, as well as pharmacologically acceptable sodium salts, pharmacologically acceptable calcium salts, pharmacologically acceptable potassium salts, lipid formulations, derivatives and/or analogs of the above.

In other aspects, the antimicrobial agent includes an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formulations; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other aspects, the antimicrobial includes an antiviral agent. Non-limiting examples of antiviral agents include cidofovir, amantadine, rimantadine, acyclovir, gancyclovir, pencyclovir, famciclovir, foscarnet, ribavirin, or valacyclovir. In some aspects the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial amino acids, peptides, or proteins. In other aspects, the polymeric coatings described herein may comprise at least one anticoagulant such as heparin, hirudin, EGTA, EDTA, urokinase, streptokinase, or hydrogen peroxide etc.

In typical aspects, the polymeric coating comprises an antimicrobial agent selected from the group consisting of chlorhexidine, octenidine, ethonium, benzalkonium chloride, benzethonium chloride, polyhexamethylene biguanide, copper, zinc, silver, chlorine, fluoroquinolones, b-lactams, macrolides, aminoglycosides, tetracyclines, and combinations thereof.

More typically, the antimicrobial agent comprises silver ions, which are typically derived from a silver salt selected from the group consisting of silver phosphate, silver citrate silver lactate, silver acetate, silver benzoate, silver chloride, silver carbonate, silver iodide, silver iodate, silver nitrate, silver laurate, silver sulfadiazine, silver sulfate, silver palmitate, and mixtures thereof.

The polymeric coatings may comprise additional agents and/or excipients as will be understood to a skilled person. For example, when silver ions are chosen as the antimicrobial agent, a dye and/or complexed silver, such as a photostabilizer (e.g., Brilliant Green) and/or pyrrolidone carboxylic acid, may be applied to the device, as is described in U.S. Pat. No. 8,877,256, which is incorporated herein by reference in its entirety. Typically, these agents are applied by soaking the device in a solution comprising the agents with or without agitation for a period of time such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes.

After the antimicrobial agent is applied to the device, the device is typically washed in a basic solution having a pH of greater than about 7.0, 7.5, 8.0, 8.5, or 9.0. The basic solution may be any known basic solution but is typically selected from the group consisting of TRIZMA base, disodium tetraborate, sodium carbonate, and hydroxides such as ammonium hydroxide, calcium hydroxide, sodium hydroxide, and mixtures thereof, for example.

In other aspects, after washing the device in ethanol, the method comprises protonating the coating. The coating is typically protonated by applying an acidic solution to the coating, wherein the acidic solution has a pH of less than about 7.0, such as less than about 6.5, less than about 6.0, less than about 5.5, less than about 5.0, less than about 4.5, or less than about 4.0, or from about 4.0 to about 7.0, such as from about 5.0 to about 6.5, such as from about 5.0 to about 6.0.

The acidic solution may be any known acidic solution, however, specific examples include acidic solutions comprising an acid selected from the group consisting of HCl, HBr, HI, HClO4, H2SO4, HNO3, sodium hydrogen sulfate, sulfonic acid, acetic acid, phosphoric acid, phosphorous acid, sulfurous acid, trichloroacetic acid, salicylic acid, phthalic acid, nitrous acid, lactic acid, hydroiodic acid, formic acid, citric acid, tartaric acid, and combinations thereof. Typically, the acidic solution comprises HCl.

The acidic solution may be applied to the coating for any period of time but typically, the device comprising the coating is soaked in the acidic solution for a time of from about 1 minute to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. In typical aspects, the device comprising the coating is soaked in the acidic solution with or without agitation for about 6 minutes.

Once the coating is protonated, an antimicrobial agent may further be added to the coating by soaking the device comprising the coating in a solution comprising the antimicrobial agent as explained above. In this way, the device will be inherently antimicrobial but will also elute an antimicrobial agent.

As noted above, the device is typically washed in ethanol after polymerization for a short period of time. This wash can assist in removing residual photoinitiator from the device and coating.

After the polymerization, protonation, and ionization steps are complete, and after any desired agents such as antimicrobial agents have been added to the coated device, the device is typically washed in deionized water for a time of from about 1 to about 30 minutes, such as from about 1, 2, 3, 4, 5, 6, 7, 8, 9, 10, 15, 20, or 25 minutes to about 2, 3, 4, 5, 6, 7, 8, 9, 10, 15, 20, 25, or 30 minutes, such as about 1, 2, 3, 4, 5, 6, 7, 8, 9, or 10 minutes. Typically, the device comprising is soaked in deionized water, with or without agitation, for a time of from about 6 to about 10 minutes.

After the wash in deionized water, the coated device is typically air dried and is optionally sterilized and packaged.

The method described above may be fully manual, fully automated, or partially automated. In particular aspects, the method is carried out substantially using the system described in International Patent Application Publication No. WO 2011/038483, which is incorporated herein by reference in its entirety, wherein the photoinitiator station described therein is modified to apply the initiator substantially only to a first side of a wall of the device, such as by aspiration into a lumen of a device, as described herein.

The methods and compositions described above are typically used to form polymeric coatings. The polymeric coatings comprise a copolymer graft-polymerized from at least one water soluble vinyl carboxylic acid monomer, as described above, and at least one water soluble neutral monomer, as described above.

In particular aspects, the vinyl carboxylic acid monomer is protonated in the polymeric coating. This is typically accomplished by soaking the polymeric coating in an acidic solution. It has been found that protonating the vinyl carboxylic acid monomer provides a coating that is inherently antimicrobial, optionally showing a greater than about 2-log reduction in microbes within about 24 hours, such as a greater than about 2-log, 3-log, 4-log, or 5-log reduction in microbes within about 5 minutes, 30 minutes, 1 hour, 2 hours, 6 hours, 12 hours, 18 hours, or 24 hours.

In alternative or additional aspects, the polymeric coating is inherently antithrombogenic, optionally showing a greater than about 80% reduction, such as a greater than about 85%, 90%, 95%, 96%, 97%, 98%, or 99% reduction, relative to an uncoated surface.

In further alternative or additional aspects, the polymeric coating releases low or no particulates, optionally releasing fewer particulates than an uncoated surface; the polymeric coating is lubricious; the polymeric coating has high resistance to cracking when expanded or inflated; and/or the polymeric coating has high resistance to delamination as demonstrated by the maintenance of hydrophilicity after exposure to high shear force. In aspects, one or more of these features are improved as compared to a polyacrylate (AA) coating.

In certain aspects, exposure of the polymeric coating to an altered pH environment, such as an acidic or basic environment, typically an acidic environment to reprotonate the surface, restores its inherent biological activity, such as antimicrobial activity, antithrombogenicity, low to no particulate release, lubricity, resistance to cracking, and/or maintenance of hydrophilicity. In aspects, one or more of these features are improved as compared to a polyacrylate (AA) coating.

The polymeric coatings described herein are typically graft-polymerized onto the surface of a medical device. The medical device is itself typically polymeric and is made from a material such as polyurethanes, polyamides, polyesters, polycarbonates, polyureas, polyethers, polyorganosiloxanes, polysulfones, polytetrafluoroethylene, polysiloxanes, or combinations thereof.

While non-limiting, the medical device is typically a device for use internally or for external use on wounds, for example. Thus, in particular aspects, the medical device is selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments. In typical aspects, the device comprises a lumen and is, for example, a catheter, stent, or tubing.

Systems for Coating

Also described herein are systems for coating devices. Such systems may comprise one or more stations for coating different reagents on devices and polymerizing coatings onto the devices. Exemplary systems are described in U.S. Pat. Nos. 8,746,168; 8,920,886; and 8,967,077, each of which is incorporated herein by reference in its entirety.

Individual stations within the system are also described. For example, an initiator station is described herein and shown in FIG. 1. The initiator station 10 comprises a tank 12 for holding the initiator 14 and a support 16, in this case a syringe, which also functions as an aspirator. The support 16 holds a device 18 in place above the initiator 14. The device 18 in this case comprises a lumen 20 that is defined by a wall 22. The wall 22 has a first side that faces out of the lumen 20 and is not directly contacted by the initiator 14. The wall 22 has a second side that faces into the lumen 20 and is contacted by the initiator 14 when it is aspirated into the lumen 20. As is shown, the support 16 holds the device 18 so that substantially only the second side of the wall 22 contacts the initiator. There may be some minor contact with the first side of the wall 22 where the end of the device 18 is slightly immersed or skims the surface of the initiator 14 so that is able to aspirate the initiator 14 into the lumen 20.

A grafting station as described in U.S. Pat. Nos. 8,746,168; 8,920,886; and 8,967,077 may also be included. The grafting station typically comprises a grafting tank for applying a polymerizable solution to the first side of the wall and a UV light source for exposing the device to UV light. Numerous other stations as described in these U.S. patents may also be included.

Figure 1:
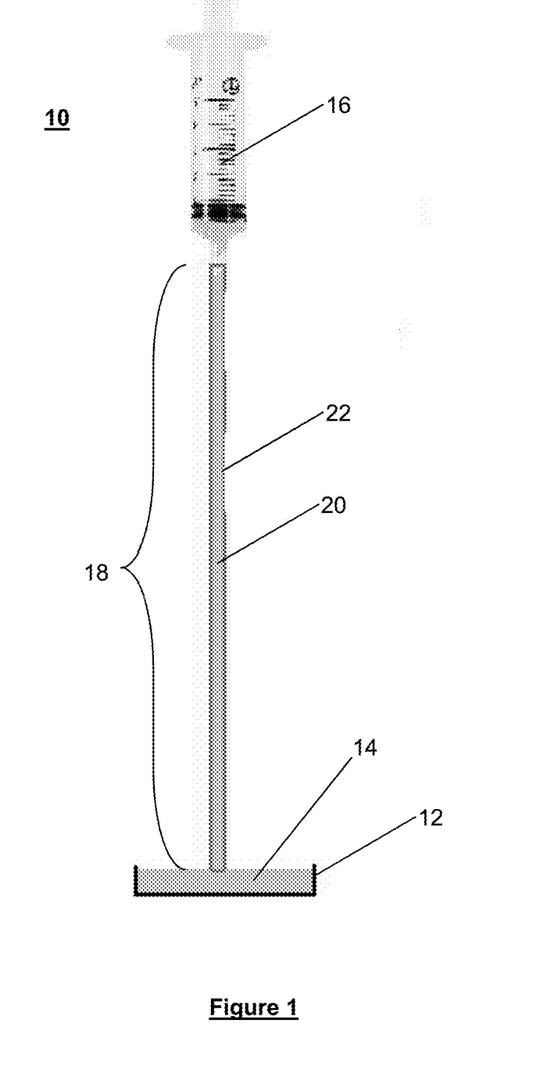
FIG. 1 shows a front view of a system as described herein.

While only a single device is shown and it is attached to a manual syringe as the aspirator, it will be understood that this method can be scaled up to hold any desired number of devices simultaneously and can transfer the devices from one tank to the next. The aspirator could be a fully integrated vacuum system. Moreover, the device need not be as shown and the system could be modified to hold other forms of devices as described herein, for example. The above-described system and method may be fully automated, partially automated, or fully manual.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Coated Polyurethane Catheter

The interior and exterior surfaces of a polyurethane (Chronoflex) vascular catheter (5 Fr) were coated with a grafted co-polymer layer according to the following method. A solution of photoinitiator complex is prepared by dissolving benzophenone and t-butylperoxybenzoate (50 mM each) in ethanol. A syringe is attached to one end of the catheter, while the other end is immersed in the photoinitiator solution. A volume of photoinitiator solution is aspirated into the catheter lumen using the attached syringe and held in place for 1 min. The lumenal solution is subsequently expelled and the treated catheter immersed in an aqueous monomer solution composed of acrylic acid and methyl acrylate (300 mM and 50 mM, respectively). Nitrogen gas is bubbled into the monomer solution for 6 min followed by exposure to UV light (350 nm) for 3 min. The catheter is then rinsed by immersion in de-ionized water for 6 min.

The presence of a co-polymeric grafted layer on both the interior and exterior surfaces of the device was confirmed by exposing the catheter to a solution of the cationic dye, Brilliant Green (1.6 mM) for 1 min. Both the interior and exterior surfaces of the catheter were stained green indicating the presence of the coating.

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method of grafting a polymeric coating onto a first side of a wall of a device, the method comprising:
    applying an initiator substantially only to a second side of the wall;
    applying a coating composition to at least the first side of the wall, wherein substantially no initiator has been applied to the first side; and
    graft-polymerizing the coating composition present on the first side of the wall and the initiator applied substantially only to the second side of the wall to form the polymeric coating on the first side of the wall.

2. The method of claim 1, further comprising applying the coating composition to the second side of the wall before the polymerizing step.

3. The method of claim 1, wherein the device comprises a lumen defined by the wall, wherein the first side of the wall faces away from the lumen and the second side of the wall faces into the lumen.

4. The method of claim 3, wherein applying the initiator substantially only to a second side of the wall comprises aspirating the initiator into the lumen and subsequently expelling the initiator from the lumen.

5. The method of claim 1, wherein the initiator is a photoinitiator selected from the group consisting of a perester, an a-hydroxyketone, a benzil ketal, a benzoin, derivatives thereof, and mixtures thereof.

6. The method of claim 1, wherein applying the coating composition to the first side of the wall comprises applying the coating composition to the first and second sides of the wall.

7. The method of claim 6, wherein applying the coating composition to the first and second sides of the wall comprises immersing the device in the coating composition.

8. The method of claim 1, wherein the coating composition comprises one or more monomers, wherein the one or more monomers comprise at least one vinyl carboxylic acid monomer and at least one neutral monomer.

9. The method of claim 8, wherein the vinyl carboxylic acid monomer is selected from the group consisting of acrylic acid, 2-bromoacrylic acid, 2-(bromomethyl) acrylic acid, 2-carboxyethyl acrylate, 2-ethylacrylic acid, itaconic acid, methacrylic acid, 2-propylacrylic acid, sodium acrylate, sodium methacrylate, 2-(trifluoromethyl) acrylic acid, and 4-vinylbenzoic acid, and combinations thereof; and, wherein the neutral monomer is selected from the group consisting of acrylates, methacrylates, acrylamides, methacrylamides, and vinyl compounds, and combinations thereof.

10. The method of claim 8, wherein the composition comprises the vinyl carboxylic acid monomer in an amount of from about 20% to about 95% by weight and/or in an amount of from about 100 mM to about 500 mM, and wherein the composition comprises the neutral monomer in an amount of from about 5% to about 80% by weight and/or in an amount of from about 10 mM to about 250 mM.

11. The method of claim 1, wherein the graft-polymerizing step comprises applying UV light to the device and optionally bubbling an inert gas through the composition, before and/or during the step of applying UV light to the device.

12. The method of claim 1, further comprising ionizing the coating after the polymerizing step.

13. The method of claim 12, further comprising applying an antimicrobial agent to the coating after the step of ionizing the coating.

14. The method of claim 13, wherein the antimicrobial agent comprises silver ions.

15. The method of claim 14, wherein the method further comprises applying a photostabilizer to the device.

16. The method of claim 13, wherein the method further comprises washing the device in a basic solution after the step of applying the antimicrobial agent.

17. The method of claim 1, further comprising protonating the coating after the polymerizing step.

18. The method of claim 1, further comprising drying and sterilizing the device.

19. The method of claim 1, wherein the coating:
a) is antimicrobial, optionally showing a greater than about 2-log reduction in microbes within about 24 hours;
b) is antithrombogenic, optionally showing a greater than about 80% reduction, relative to an uncoated surface;
c) releases low or no particulates, optionally releasing fewer particulates than an uncoated surface;
d) is lubricious;
e) has high resistance to cracking when expanded or inflated; and/or
f) has high resistance to delamination and maintains hydrophilicity after exposure to high shear force.

20. The method of claim 19, wherein exposure of the polymeric coating to an altered pH environment restores the antimicrobial activity, the antithrombogenicity, the low to no particulate release, the lubricious property, the resistance to cracking, and/or maintenance of hydrophilicity.

21. The method of claim 1, wherein the device is made from a material selected from the group consisting of polyurethanes, polyamides, polyesters, polycarbonates, polyureas, polyethers, polyorganosiloxanes, polysulfones, polytetrafluoroethylene, polysiloxanes, and combinations thereof; and, wherein the device is a medical device selected from the group consisting of dressings, sutures, scaffolds, fracture fixation devices, catheters, stents, implants, tubings, rods, prostheses, electrodes, endoscopes, cardiac valves, pacemakers, dental implants, and surgical, medical or dental instruments.

22. The method of claim 1, wherein the polymeric coating comprises a copolymer.

* * * * *

UNITED STATES PATENT AND TRADEMARK OFFICE
CERTIFICATE OF CORRECTION

PATENT NO. : 12,180,386 B2
APPLICATION NO. : 16/900332
DATED : December 31, 2024
INVENTOR(S) : Vyacheslav Dudnyk et al.

Page 1 of 1

It is certified that error appears in the above-identified patent and that said Letters Patent is hereby corrected as shown below:

In the Claims

In Column 14, Line 30, Claim 5, delete "a-hydroxyketone," and insert -- α-hydroxyketone, --, therefor.

Signed and Sealed this
Twenty-second Day of April, 2025

Coke Morgan Stewart
*Acting Director of the United States Patent and Trademark Office*